United States Patent
Marquant

(10) Patent No.: US 7,638,023 B2
(45) Date of Patent: Dec. 29, 2009

(54) CAPILLARY BIOSENSOR ANALYSIS SYSTEM

(75) Inventor: Michael Marquant, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1037 days.

(21) Appl. No.: 11/088,305

(22) Filed: Mar. 24, 2005

(65) Prior Publication Data

US 2005/0230253 A1 Oct. 20, 2005

Related U.S. Application Data

(63) Continuation of application No. PCT/EP03/10378, filed on Sep. 18, 2003.

(30) Foreign Application Priority Data

Sep. 26, 2002 (DE) ................................ 102 44 775

(51) Int. Cl.
*G01N 27/327* (2006.01)
*G01N 21/00* (2006.01)

(52) U.S. Cl. .................................. 204/403.02; 422/58

(58) Field of Classification Search ................................
204/403.01–403.15; 205/777.5, 778, 792;
422/55–58
See application file for complete search history.

(56) References Cited

U.S. PATENT DOCUMENTS

| | | | |
|---|---|---|---|
| 4,088,448 A | 5/1978 | Lilja et al. | |
| 5,047,044 A | 9/1991 | Smith et al. | |
| 5,395,504 A | 3/1995 | Saurer et al. | |
| 5,437,999 A | 8/1995 | Diebold et al. | |
| 5,609,823 A | * 3/1997 | Harttig et al. | ................. 422/66 |
| 5,757,666 A | 5/1998 | Schreiber et al. | |
| 5,797,693 A | 8/1998 | Jaeger | |
| 5,802,940 A | 9/1998 | Jaeger | |
| 6,027,689 A | 2/2000 | Markart | |
| 6,071,391 A | 6/2000 | Gotoh et al. | |

(Continued)

FOREIGN PATENT DOCUMENTS

DE 197 14 674 A1 10/1998

(Continued)

OTHER PUBLICATIONS

EPO English language machine translation of the Description of DE 19819407 A1. Translation obtained Mar. 23, 2009.*

*Primary Examiner*—Alex Noguerola
(74) *Attorney, Agent, or Firm*—Justin L. Sage; Roche Diagnostics Operations, Inc.

(57) ABSTRACT

A capillary biosensor analysis system is provided for analyzing a liquid sample, comprising a plurality of longitudinally arranged and consecutively provided and aligned capillary biosensors having a capillary channel enclosed by at least two wall parts and containing one or more reagents, and an evaluation instrument which has a holder to position a forward-most capillary biosensor in a measurement position for performing an analysis. The plurality of capillary biosensors are implemented as a multiple capillary-biosensor strip. A multiple capillary-biosensor strip is guided and held in the holder in such a manner that one capillary biosensor of the strip at a time is located in the measurement position. The multiple capillary-biosensor strip is movable in the evaluation instrument in such a manner that consecutive capillary biosensors of the multiple capillary-biosensor strip are transported one after the other into the measurement position.

38 Claims, 4 Drawing Sheets

U.S. PATENT DOCUMENTS

| | | | |
|---|---|---|---|
| 6,103,033 A | 8/2000 | Say et al. | |
| 6,284,125 B1 * | 9/2001 | Hodges et al. | 205/775 |
| 6,484,045 B1 * | 11/2002 | Holker et al. | 600/345 |

FOREIGN PATENT DOCUMENTS

| | | |
|---|---|---|
| DE | 198 19 407 A1 | 11/1999 |
| EP | 0 299 517 A2 | 1/1989 |
| EP | 0 057 110 B2 | 1/1990 |
| EP | 0 826 963 A2 | 3/1998 |
| EP | 1 114 995 | 7/2001 |
| GB | 2 090 659 A | 7/1982 |
| JP | 2000-258382 | 9/2000 |
| WO | WO 86/00138 A1 | 1/1986 |
| WO | WO 99/32881 A1 | 7/1999 |

\* cited by examiner

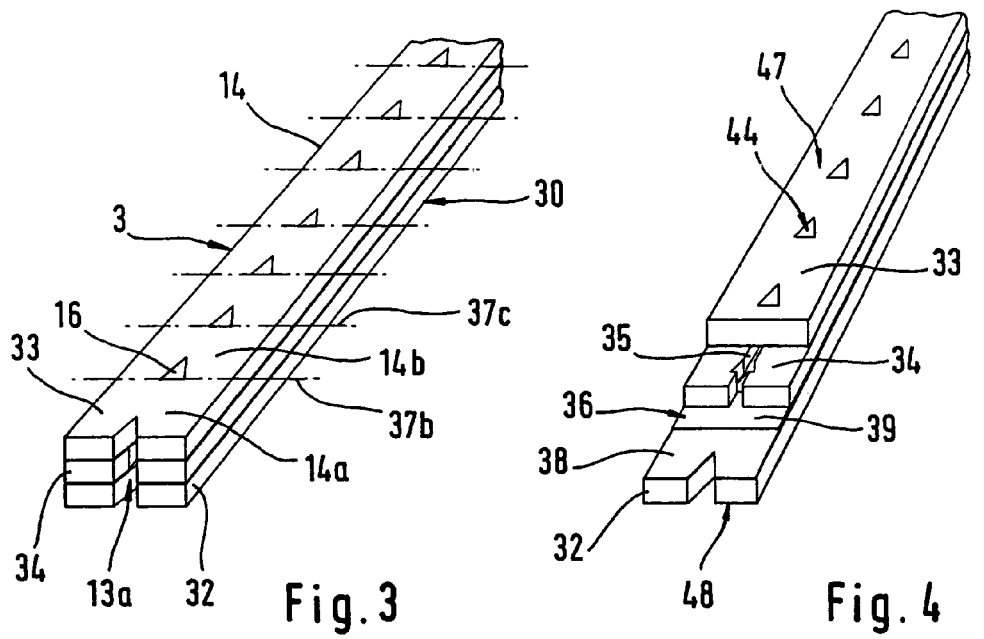
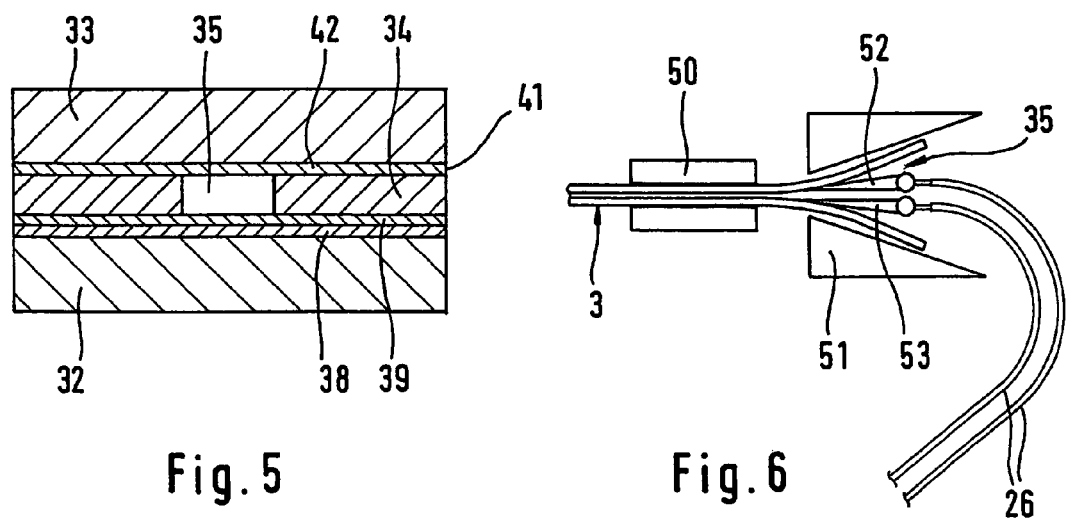

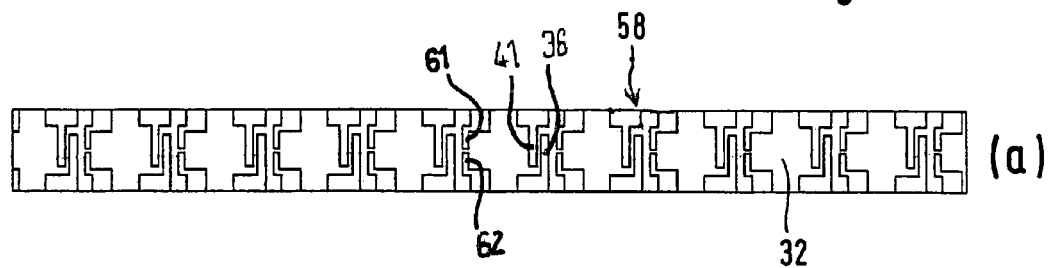
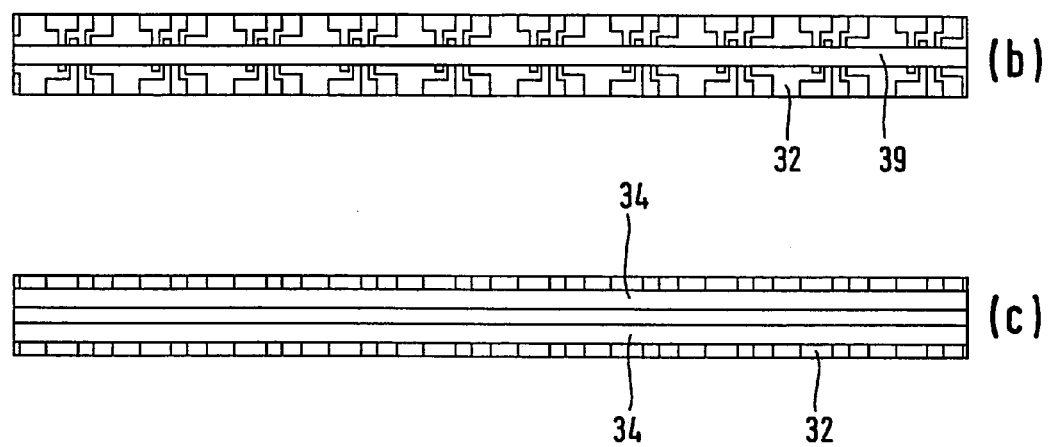
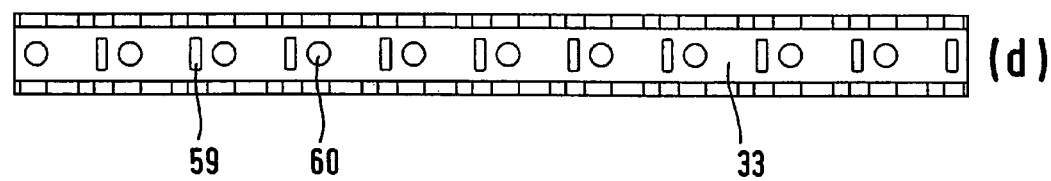
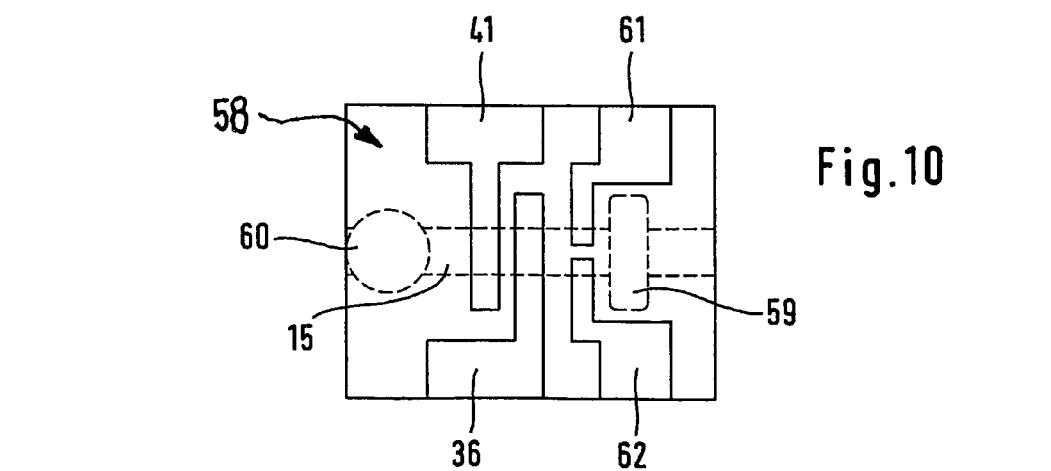
Fig. 9
Fig. 10

CAPILLARY BIOSENSOR ANALYSIS SYSTEM

This application is a Continuation claiming the benefit of Patent Cooperation Treaty Application No. PCT/EP2003/10378 entitled "Capillary Biosensor Analysis System", filed on Sep. 18, 2003, which claims the benefit of German Application No. DE 102 44 775.6 entitled "Capillary Biosensor Analysis System", filed on Sep. 26, 2002, the entire disclosures of each of which are hereby incorporated by reference herein.

BACKGROUND OF THE INVENTION

The present invention relates to a capillary biosensor analysis system for analyzing a sample liquid for an analyte contained therein as well as a multiple measurement capillary biosensor strip suitable as a component of such a system.

BRIEF DESCRIPTION OF THE PRIOR ART

Analysis systems, which include analysis elements intended for one-time use and evaluation instruments tailored to a specific type of analysis element, are used to a large extent for the qualitative and quantitative analysis of components of liquid samples, in particular bodily fluids of humans and other animals. To perform an analysis, the analysis element, which is also referred to as a "biosensor", is brought into contact with the sample. The reaction of the sample with at least one reagent contained in the biosensor results in a change of a measurable physical property (measurement variable) of the biosensor, which is characteristic for the analysis. The evaluation instrument contains an electrical measurement and evaluation device for measuring the measurement variable and determining the desired analysis information (typically the concentration of the analyte) on the basis of the measured value.

Capillary biosensors have been previously provided which have a capillary channel, enclosed by at least two wall parts, having an inlet for the sample liquid and a vent. The capillary channel contains the reagents required for the analysis. During use of these capillary biosensors, a drop of the sample liquid (such as blood) is brought into contact with the inlet and drawn by capillary forces into the capillary channel, where the reaction that is characteristic for the desired analysis occurs.

Analysis systems can be designed for analysis by, for example, calorimetric or electrochemical (e.g. amperometric or potentiometric) techniques. Examples of colorimetric capillary biosensors are described in the following publications: U.S. Pat. No. 4,088,448; GB 2 090 659 A; and EP 0 057 110.

In the field of conventional colorimetric analysis elements, which are generally provided without a capillary channel, several design proposals have already been made where a plurality of analysis elements are assembled into a strip. For example, the publication EP 0 299 517 A2 describes an analysis system in which a band-shaped analysis film is used, which contains a plurality of multilayered analysis elements. In the instrument the band-shaped analysis film is kept ready on a first spool and wound onto a second spool after use. A similar design is described in DE 198 19 407 A1.

Examples of multiple-biosensor strips which comprise an arrangement of calorimetric analysis elements connected to one another in series are known from the publications U.S. Pat. No. 5,757,666; DE 197 14 674 A1; and U.S. Pat. No. 6,027,689. These designs are, however, not suitable for capillary biosensors, in which specific problems arise which result, for example, from the integration of the capillary channel, the requirements of the manufacturing process connected therewith, and the requirements of use (e.g., accessibility of the inlet opening).

An example of electrochemical capillary biosensors is described in the publication WO 86/00138. In this case, the capillary channel contains at least two electrodes (working electrode and counter electrode) and the reagents are selected so that as a result of the analysis reaction, a change (of a current or a voltage) occurs, which is electrically measurable by means of the electrodes. In order to provide the required connection to the evaluation instrument, these capillary biosensors have contacts which are connected to the electrodes on one side and, when the capillary biosensor is plugged into the evaluation instrument, to corresponding instrument contacts on the other side, thus providing an electrical connection to the electrical measurement and evaluation device of the evaluation instrument. Other examples of such electrochemical capillary biosensors are described in the following publications: U.S. Pat. No. 5,437,999; WO 99/32881; U.S. Pat. No. 6,103,033; Patent Abstract of Japan 2000-258382; U.S. Pat. No. 6,071,391.

SUMMARY OF EMBODIMENTS OF THE INVENTION

Embodiments of the present invention contemplate a capillary biosensor analysis system wherein the capillary biosensors are provided in a multiple capillary-biosensor strip. A plurality of capillary biosensors are positioned longitudinally one after the other in the multiple capillary-biosensor strip. Each strip is guided and held in a holder in the evaluation instrument in such a manner that only the inlet of the forward-most capillary biosensor of the strip is accessible for contact with sample liquid, and the strip is movable within the evaluation instrument so that consecutive capillary biosensors of the strip are transported one after the other into a measurement position.

Certain embodiments of the disclosed system may operate with electrochemical capillary biosensors. In one embodiment, simple handling is achieved by including a cutting device with the evaluation instrument. As such, after each measurement with the forward-most capillary biosensor, the so-used capillary biosensor is cut off or otherwise removed from the multiple capillary-biosensor strip.

The present invention will be explained in greater detail hereafter on the basis of exemplary embodiments schematically illustrated in the Figures. The features shown therein may be used individually or in combination to provide preferred embodiments of the present invention.

BRIEF DESCRIPTION OF THE DRAWINGS

FIG. 3 shows a perspective view of an embodiment of a multiple capillary-biosensor strip.

FIG. 4 shows a partially cutaway perspective view of an embodiment of a multiple capillary-biosensor strip.

FIG. 5 shows a cross-section through an embodiment of a multiple capillary-biosensor strip.

FIG. 6 shows an illustration of an embodiment of electrical connection between a multiple capillary-biosensor strip and an electrical measurement and evaluation device.

FIG. 9 shows an illustration of an embodiment of the layout of different layers of a multiple capillary-biosensor strip for use in a system according to FIG. 8.

FIG. 10 shows a detail view of an embodiment of the electrode arrangement of FIG. 9.

DETAILED DESCRIPTION OF EMBODIMENTS OF THE INVENTION

Although the disclosure hereof is detailed and exact in order to enable those skilled in the art to practice the invention, the physical embodiments herein disclosed merely exemplify the invention which may be embodied in other specific structure. The scope of the invention is defined in the claims appended hereto.

Figure 1:
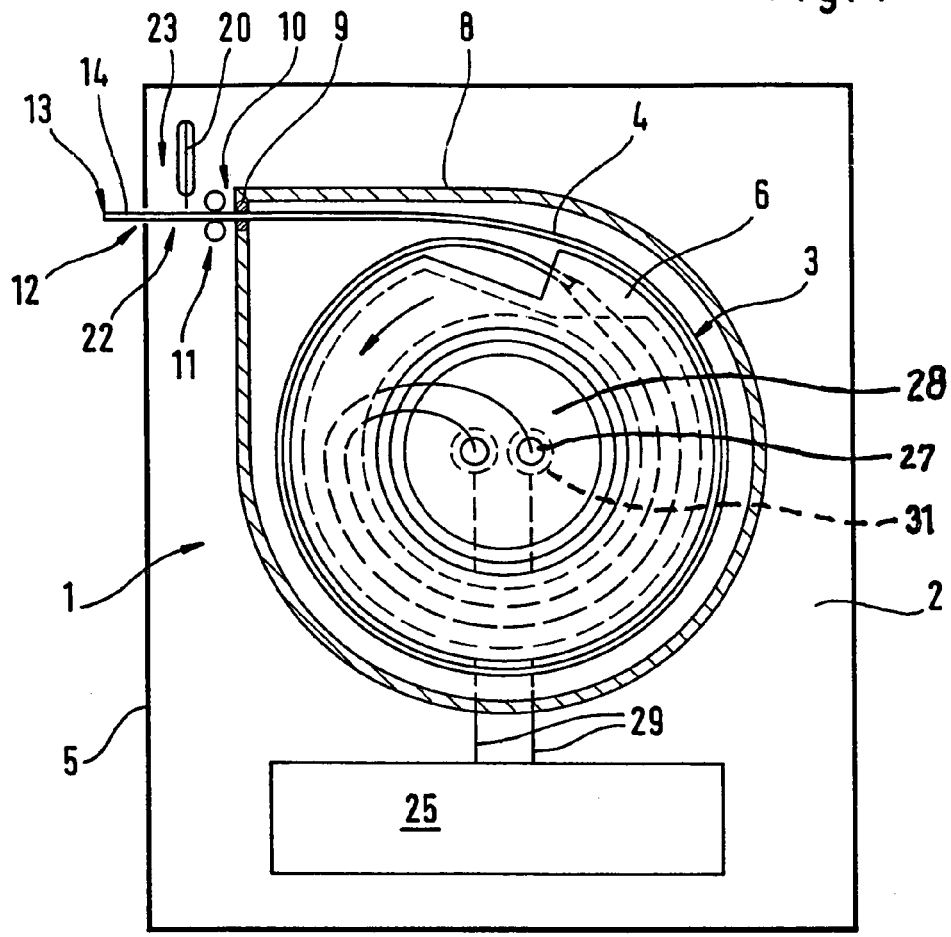
FIG. 1 shows a capillary biosensor analysis system according to an embodiment of the present invention in a side view, partially as a block diagram.

The capillary biosensor analysis system 1 shown in FIG. 1 comprises an evaluation instrument 2 and a multiple capillary-biosensor strip 3, which may be removably inserted into the evaluation instrument 2. In the embodiment shown, the multiple capillary-biosensor strip 3 is implemented as a resiliently flexible band 4, which is wound up in a curved state on a generally hollow rotatable drum 6.

The band 4 and the drum 6 are located inside a sealed cassette 8, which may be removably inserted into the evaluation instrument 2. The front end of the band 4 projects out of the cassette 8 through an outlet opening 10, provided with flexible seals 9. The band 4 is clamped between two transport rollers 11 and projects out of an aperture 12 of the housing 5 in such a manner that an inlet 13 provided at the front edge of the multiple capillary-biosensor strip 3 is accessible, so that it may be contacted with a sample liquid 19.

Figure 2:
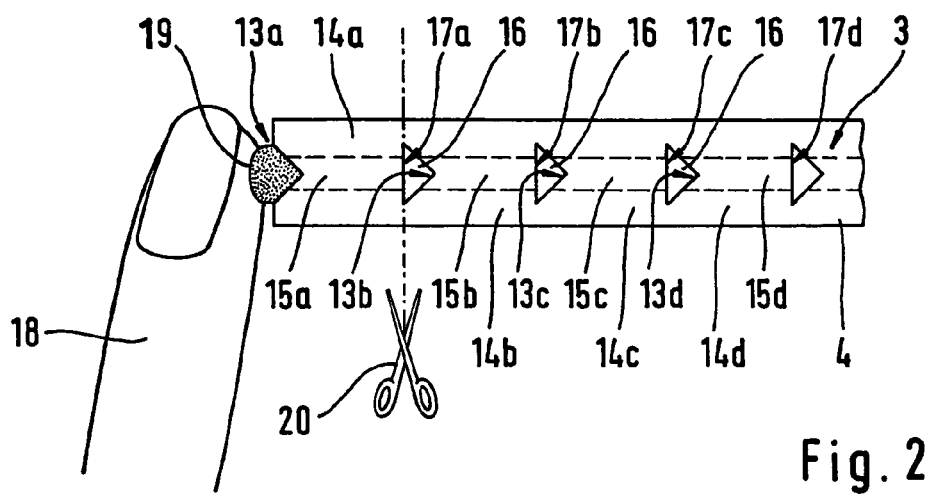
FIG. 2 shows an embodiment of a multiple capillary-biosensor strip while an exemplary blood sample is being applied.

FIG. 2 shows a schematic diagram illustrating a sampling procedure for an embodiment of the invention. In this embodiment, the multiple capillary-biosensor strip 3, shown in plan view, comprises a plurality of individual capillary biosensors 14a-14d, arranged longitudinally one after the other, which are defined by consecutive sections of the band 4. As shown, the capillary biosensors 14a-14d each comprise a respective capillary channel 15a-15d, each having a respective inlet 13a-13d for the sample liquid 19 and a respective vent 17a-17d.

Reference throughout this disclosure (both supra and infra) to only four biosensors 14a-14d and respective components 13a-13d, 15a-15d and 17a-17d etc. is by means of example only and is in no way intended to limit the possible number of biosensors 14 in a strip 3 to only four or even to require as many as four. Various embodiments may have as many or few biosensors 14 as desired. Similarly, any reference to biosensor 14a as the forward-most biosensor 14 is for purposes of example and convenience only, and the person of ordinary skill in the art will appreciate that each successive biosensor 14b-14zz may become the forward-most biosensor 14 at such time as the preceding biosensor 14 is removed from the strip 3 as provided herein according to various embodiments of the present invention.

In one embodiment, the capillary channels 15a-15d of the capillary biosensors 14a-14d run in the longitudinal direction of the multiple capillary-biosensor strip 3 and are provided one after the other and in alignment in such a manner that the inlet 13 of each following capillary biosensor 14 (e.g. inlet 13b for biosensor 14b) and the vent 17 of the immediately preceding capillary biosensor 14 (e.g. vent 17a for biosensor 14a) are located diametrically oppositely in such a way as to face one another. Separation between the capillary channels 15 in other embodiments is achieved by means of flow obstructions 44, which comprise, in one embodiment, apertures 16 that penetrate the entire sensor strip 3 and extend over at least the entire width of the capillary channel 15. The apertures 16 in such an embodiment simultaneously form the inlets 13b-13d and the vents 17a-17d.

Embodiments of a multiple capillary-biosensor strip 3 may, as will be explained in greater detail below, be manufactured simply in a continuous method. In one embodiment, all production steps can be performed on a band 4 running in the lengthwise direction of the strip 3. In other embodiments, no motions transverse to the production direction are necessary.

In order to perform an analysis, a drop of sample liquid 19, for example a blood drop obtained by pricking a finger 18, is brought into contact with the inlet 13a of the forward-most capillary biosensor 14a of the multiple capillary-biosensor strip 3 in such a manner that the sample liquid is drawn into the capillary channel 15a by capillary forces. When a capillary channel 15 has been filled, the reaction with one or more reagents contained therein (for example, in reagent layer 39 discussed further below) takes place and subsequently the measurement of a measurement variable that is characteristic for the desired analysis is performed. Embodiments of the present invention do not materially differ from known capillary biosensors with respect to the biochemical and/or electrochemical analysis methods used, so that no further explanation thereof is necessary for those of ordinary skill in the art. Similarly, the electrical measurement and evaluation device 25 of the instrument 2 is configured to perform measurements and make calculations based thereon for purposes of determining an analyte concentration in a manner not materially different with respect to devices typically employed in conjunction with such biochemical and/or electrochemical analysis methods, so that no further explanation of the operations and capabilities of such devices is necessary for those of ordinary skill in the art.

After performing the measurement, the used forward-most capillary biosensor 14a in one embodiment is cut off, for example by means of a cutting device 20, from the multiple capillary-biosensor strip 3, and disposed of. Subsequently, the multiple capillary-biosensor strip 3 is extended further using the transport rollers 11, so that the next-following capillary biosensor 14b is brought into the measurement position 22. As shown in the embodiment of FIG. 1, the cassette 8 and the transport rollers 11 define a capillary biosensor holder 23, in order to position one capillary biosensor 14 at a time in the measurement position 22 in such a manner that its inlet 13 is accessible, so that a liquid sample 19 can be contacted with it in such a manner that the sample liquid 19 is drawn by capillary forces into the capillary channel 15 and fills it. The multiple capillary-biosensor strip 3 is guided and held in the capillary biosensor holder 23 in such a manner that in each case the forward-most capillary biosensor 14a of the strip 3 is located in the measurement position 22, in which its inlet 13a is accessible for contact with sample liquid 19. The strip 3 is movable inside the evaluation instrument 2 in such a manner that consecutive capillary biosensors 14 are extended one after the other into the measurement position 22.

The embodiment of a multiple capillary-biosensor strip 3 illustrated in FIG. 1 comprises a series of electrochemical capillary biosensors 14 having electrodes 36, 41 which must be connected to an electronic measurement and evaluation device 25 to perform a measurement. For this purpose, in one embodiment the electrodes (as will be explained further below) are electrically connected to one end of conductive leads 26 wound up inside the hollow drum 6. In other embodiments, the other ends of conductive leads 26 are electrically connected, such as by soldering, to corresponding contacts 27 located on an internal surface 28 of the cassette 8. The contacts 27 extend to the external surface of the cassette 8 and, when the cassette 8 is inserted into the evaluation instrument 2, the contacts 27 are connected to corresponding device contacts 31 (shown dashed in FIG. 1), which are in turn connected to the electronic measurement and evaluation device 25 via fixed lines 29 in the instrument 2. The length of the conductive leads 26 is so dimensioned that the sensor strip 3 may be wound up completely and unwound completely during use.

Details of construction of the multiple capillary-biosensor strip 3 according to the present invention may be seen more clearly in FIGS. 3 to 5. The multiple capillary-biosensor strip 3 illustrated therein may be embodied as generally flat and straight elongated rod 30. However, if flexible materials of relatively low thickness are used, a flexible band 4, as shown in FIG. 1, may also be designed using the same principles in order to enable the band 4 to be wound and unwound upon drum 6.

Structural elements of the construction of one embodiment shown comprise a lower tape 32, an upper tape 33, and two spacer tapes 34 with adhesive on both sides. The tapes 32 and 33 may be fixedly spaced apart by means of spacer tapes 34 at the desired distance from one another in such a manner that a continuous capillary channel 35 is formed. In one embodiment, the continuous capillary channel 35 is divided by the apertures 16 into the individual capillary channels 15a-15d of the respective capillary biosensors 14a-14d. Continuous channel 35 is generally delimited on the top and bottom by the tapes 32, 33 and laterally by the spacer tapes 34. In other embodiments, the tapes 32, 33, 34 are made of plastic materials as typically used in biosensor technology, such as polyester or polyamide.

In the embodiments illustrated in FIGS. 3-6, the working electrode 36 of the sensors 14 (whose separation lines 37 are indicated dashed in FIG. 3) are formed by a layer 38 of a conductive material. In one embodiment, layer 38 is vapor-deposited onto the lower tape 32. Similarly, the counter electrode 41 is provided on the upper tape 33 by, for example, vapor-depositing. In other embodiments, a reagent layer 39 is provided above the conductive layer 38 in such a position to be exposed within the continuous channel 35. Reagent layer 39 contains the necessary reagent(s) corresponding to a particular analyte measurement for a particular liquid sample 19. For example, to determine glucose, typically the enzyme glucose oxidase and optionally a suitable mediator are provided in the reagent layer 39. In yet other embodiments, the conductive layer 38 is made of a metal, such as gold, silver, palladium, or platinum, or of graphite. In yet other embodiments, the counter electrode 41 may be formed, for example, by a Ag/AgCl layer 42, which is only shown in FIG. 5.

A construction of this type may be manufactured cost-effectively as an endless band 4 using coating and bonding techniques used for manufacturing typical biosensors. First the tapes 32 and 33 are coated with the layers 38, 39 and/or 42 and then are assembled together using the spacer tapes 34 having adhesive on both sides.

In one embodiment, after the tape-layered strip 3 is assembled, the apertures 16 are stamped in, each of which forms a flow obstruction 44 in the continuous capillary channel 35. By these flow obstructions 44, the flow of a sample liquid 19 penetrating through inlet 13a into the channel 15a of the forward-most capillary biosensor 14a is stopped and the sample liquid 19 is reliably prevented from penetrating into the inlet 13b of the next following capillary biosensor 14b in the multiple capillary-biosensor strip 3. At the same time, the displaced air escapes through the vent 17a defined by aperture 16, which simultaneously defines the vent 17a of capillary biosensor 14a and (after the forward-most capillary biosensor 14a is cut off along the separation line 37b) defines the inlet 13b of the next following capillary biosensor 14b. In the embodiment shown, manufacturing is also simplified by the fact that the position in the lengthwise direction relative to each other of the tapes 32, 33, 34 assembled to form the tape-layered strip 3 is not important in the production process.

In other embodiments, apertures 16 penetrate at least the upper tape 33 and such portion of the spacer tapes 34 necessary to ensure that the apertures extend over the entire width of the continuous capillary channel 35. In yet other embodiments, apertures 16 further penetrate the lower tape 32. In yet other embodiments, a flow obstruction 44 may be provided by other means, such as making the appropriate section of each capillary channel 15a-15d hydrophobic, such as the section around or proximate to the vents 17a-17d. In this manner, liquid sample 19 is prevented from flowing through a vent 17 whereas displaced air is still permitted to escape through the vent 17. Such a vent 17 may also be defined, for example, by a vent hole (not shown) located in the upper tape 33 proximate the downstream end of the channel 15 of each biosensor 14.

In one embodiment, the wall parts 47, 48, which comprise upper and lower tapes 33, 32 and which delimit the capillary channels 15 of the capillary biosensors 14, are formed by flat films having non-profiled surfaces and extend over the entire length of the multiple capillary-biosensor strip 3. In other embodiments, a high flexibility may be achieved by the selection of the materials for the wall parts 47, 48 so that the capillary biosensor strips 3 may be wound up with a low radius of curvature and thus integrated into the analysis system 1 in a space-saving manner. The multiple capillary-biosensor strips 3 may in principle, however, also be manufactured from parts with profiled surfaces, such as deep-drawn profiled films. In other embodiments, the profiling is not be so pronounced that the desired flexibility is no longer achieved.

In any case, the wall parts 47, 48 which enclose the continuous capillary channel 35 (and, thereby, the channels 15) are typically made of plastic film bands, which in one embodiment are drawn off from rolls (not shown) and may be assembled together in a continuous method in such a manner that the continuous capillary channel 35 remains between them. In other embodiments, the separation of the continuous capillary channel 35 into the channels 15 of consecutive capillary biosensors 14 may also be achieved—instead of by the apertures 16—by spacer strips 34 applied in the course of the manufacturing process which not only run along the lengthwise edges of the strip 3 between tapes 32,33, but also have transverse webs (not shown) extending between them, by which the capillary channels 15 of the individual sensors 14 may be separated from one another. In this case venting may be provided by a vent hole (not shown) located in the upper tape 33 proximate the downstream end of the capillary channel 15 of each biosensor 14.

Referring now to FIGS. 1 and 6, in one embodiment, the electrodes formed by the conductive layer 38 and/or the conductive layer 42 each extend without electrical separation over all capillary biosensors 14 of the multiple capillary-biosensor strip 3 and are connected via conductive leads 26 to corresponding contacts 27 and thus to the electronic measurement and evaluation device 25 of the evaluation instrument 2. FIG. 6 shows one embodiment for providing suitable construction of the electrical contact between the multiple capillary-biosensor strip 3 and the conductive leads 26 leading to the electronic measurement and evaluation device 25. During assembly the multiple capillary-biosensor strip 3 is pushed into a guide 50, which may be a component of the drum 6 shown in FIG. 1. When the strip 3 penetrates into a contacting device 51, two wedge-shaped contact edges 52, 53, which are positioned opposite to one another and are electrically insulated from one another, penetrate into the continuous capillary channel 35 of the strip 3, split it open separating the upper and lower tapes 33, 32, and at the same time contact their respective conductive interior walls comprising layers 42, 38. The two contact edges 52, 53 are connected to the conductive leads 26.

Figure 7:
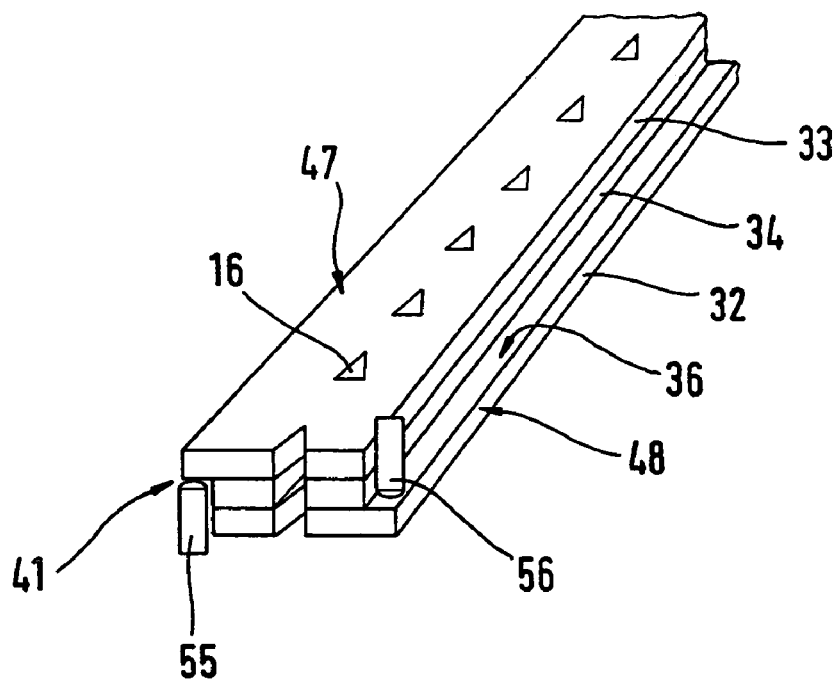
FIG. 7 shows a perspective illustration of an alternative embodiment of a multiple capillary-biosensor strip having sliding contacts.

The embodiment of the multiple capillary-biosensor strip 3 shown in FIG. 7 differs from the embodiment shown in FIGS. 3 to 5 in that the electrical contact to the electrodes 36, 41 is provided by means of sliding contacts 55, 56 which are fixed to the instrument 2 and are in direct electrical contact with the corresponding electrodes 36, 41, as shown, at the lateral edges thereof which are left partially exposed by the upper and lower tapes 33, 32 being slightly laterally offset during manufacture.

In the alternative embodiment shown in FIGS. 9 and 10, discrete two-dimensional electrode structures in a common plane are used instead of continuous electrode layers extending over the entire surface in opposing arrangement. Such a multiple capillary-biosensor strip 3 may also be embodied as a tape-layered construction having three structural layers, where the wall parts 47, 48, which delimit the capillary channel 35 on top and bottom, can be formed from film tapes.

The layout of the layers in this embodiment is shown in FIG. 9. Partial FIGS. 9a, 9b, and 9c show plan views of the lower tape 32 in three manufacturing steps. Partial FIG. 9a shows a plurality of conductor structures 58 for defining the electrodes 36, 41. A reagent layer 39 running over a portion of each conductor structure 58 is shown in partial FIG. 9b. Partial FIG. 9c shows the lower tape 32 after two spacer tapes 34 have been positioned. Finally, partial FIG. 9d shows an upper tape 33 having holes 59 and 60 which may be punched out or otherwise formed into the upper tape 33. Holes 60 are used for sample supply inlets and holes 59 are used as vents. In one embodiment, vent holes 59 simultaneously form flow obstructions, by which the flow along the capillary channel 15 of each biosensor 14 is stopped and the sample liquid 19 is prevented from penetrating into the neighboring capillary biosensor 14. To this end it is sufficient to provide holes 59 which penetrate at least the upper tape 33 through to the capillary channel 15 of each biosensor 14 in the strip 3, and which extend over the entire width of the capillary channel 15. In other embodiments, both the vent holes 59 and the holes 60 used for the sample supply inlets may extend through both wall parts 47, 48, i.e., through the entire strip 3 for each capillary biosensor 14.

As may be seen more clearly from FIG. 10, in one embodiment control electrodes 61, 62, in addition to the working electrode 36 and the counter electrode 41, are provided in the conductor structure 58 which may, for example, be used to electrically check the filling status of the corresponding capillary channel 15. FIG. 10 also shows (dashed) the preferred position of the holes 59 and 60 for each biosensor 14. When a liquid sample 19, such as a blood drop, is brought into contact with the hole 60 used as the sample supply inlet, it is drawn into the capillary channel 15, contacting the electrodes 36 and 41 first. As it penetrates further, the sample 19 contacts the control electrodes 61, 62. This causes a change in the electrical resistance between these electrodes 61, 62. This resistance change may be measured by device 25 in known manner as an indication that the capillary channel 15 is filled up to the region of the control electrodes 61, 62 and thus sufficient sample 19 in contact with the working electrode 36 and the counter electrode 41 is ensured. In order to provide this function, the control electrodes 61, 62 must be positioned between the electrodes 36, 41 on one side (upstream) and the vent hole 59 on the other side (downstream). The relatively complex electrode structure shown may be produced efficiently in a continuous ablation process. In one embodiment, the ablation process comprises a laser ablation process.

Figure 8:
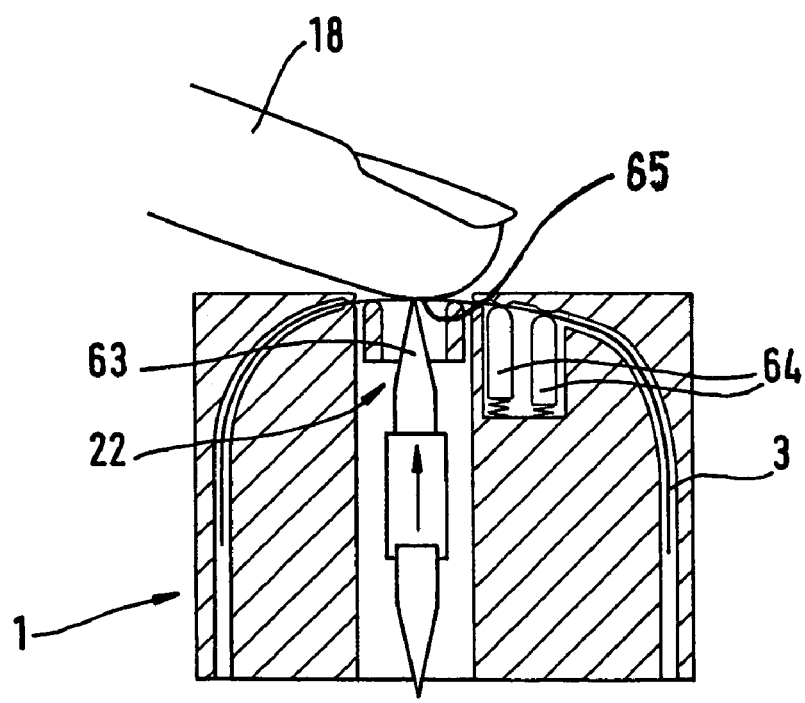
FIG. 8 shows a schematic diagram of an alternative embodiment of a capillary biosensor analysis system according to an embodiment of the present invention.

Referring now to the embodiment of an analysis system 1 schematically shown in FIG. 8, a multiple capillary-biosensor strip 3 is moved continuously step-by-step past the measurement position 22. At the measurement position 22, a mechanically movable lancet 63 is provided, which pricks the finger 18. The blood drop thus obtained penetrates through a hole 65 into the capillary biosensor 14 located in the measurement position 22. The resulting electrical signal is carried by the electrodes 36, 41 which are tapped via electrode contacts 64 and the signal is fed to the electrical measurement and evaluation device 25. The embodiment of the multiple capillary-biosensor strip 3 used here may be designed as shown in FIGS. 9 and 10, but may also have a design having reagent layers 39 and opposing electrode layers 38, 42 over the entire surface, as is shown in FIGS. 3 through 5. In any case, the hole 65 used as the sample supply inlet must extend through all layers of the biosensor strip 3, so that the lancet 63 may pierce through this hole 65 into the finger 18.

A sensor in which the lancets are integral components of the sensor construction is known from U.S. Pat. No. 5,047,044. However, this requires that the sensor is made from complexly-shaped molded parts, having many individual elements. Such a design may in practice only be manufactured by an injection molding process. In relation thereto, the design shown in FIGS. 8 and 10 is much simpler and more cost-effective.

While several versions have been disclosed herein, it is to be understood that the versions and variations shown and described are merely illustrative of the principles of the invention and that various modifications may be implemented by those skilled in the art without departing from the scope and spirit of the invention and the claims appended hereto:

What is claimed is:

1. A multiple capillary-biosensor strip for an analysis system adapted for analyzing a sample liquid, said strip comprising:
 a plurality of capillary biosensors arranged longitudinally along the strip and consecutively provided one after the other, each said biosensor including a capillary channel delimited by at least two wall parts and having an inlet on one end thereof for drawing the sample liquid therein by capillary forces and a vent, the capillary channel of each said biosensor containing at least one reagent, the reaction of the sample liquid with the at least one reagent resulting in a measurable change of a measurement variable which is characteristic for the desired analysis of the sample liquid.

2. The multiple capillary-biosensor strip according to claim 1, wherein the wall parts are formed from at least two tapes.

3. The multiple capillary-biosensor strip according to claim 1 or claim 2, said strip being implemented as a resiliently flexible band adapted for being wound up in a curved state for being removably inserted into an evaluation instrument.

4. The multiple capillary-biosensor strip according to claim 3, the capillary channels for the consecutively provided biosensors generally being in alignment such that the inlet for a following said biosensor generally oppositely faces the vent for the biosensor preceding said following biosensor, the strip further comprising a plurality of spaced apart flow obstructions provided on at least one of the wall parts, each flow obstruction being provided in conjunction with at least one capillary channel and proximate each vent-inlet interface, each said flow obstruction being configured to obstruct the flow of sample liquid through each capillary channel proximate its respective vent to prevent flow from continuing into the inlet of the following biosensor.

5. The multiple capillary-biosensor strip according to claim 4, wherein the flow obstruction comprises an aperture extending through at least one of the wall parts and over the width of the capillary channel.

6. The multiple capillary-biosensor strip according to claim 5, each said biosensor comprising an electrochemical capillary sensor having a working electrode, a counter electrode, and means for electrically connecting the working and counter electrodes to an evaluation instrument configured for measuring the measurement variable.

7. The multiple capillary-biosensor strip according to claim 6, wherein said working electrode comprises a first electrically conductive layer extending over a capillary-channel facing surface of one said wall part, and said counter electrode comprises a second electrically conductive layer extending over a capillary-channel facing surface of the other said wall part, each said layer being electrically isolated from the other along the multiple capillary-biosensor strip.

8. The multiple capillary-biosensor strip according to claim 3, each said biosensor comprising an electrochemical capillary sensor having a working electrode, a counter electrode, and means for electrically connecting the working and counter electrodes to an evaluation instrument configured for measuring the measurement variable.

9. The multiple capillary-biosensor strip according to claim 8, wherein said working electrode comprises a first electrically conductive layer extending over a capillary-channel facing surface of one said wall part, and said counter electrode comprises a second electrically conductive layer extending over a capillary-channel facing surface of the other said wall part, each said layer being electrically isolated from the other along the multiple capillary-biosensor strip.

10. The multiple capillary-biosensor strip according to claim 4, each said biosensor comprising an electrochemical capillary sensor having a working electrode, a counter electrode, and means for electrically connecting the working and counter electrodes to an evaluation instrument configured for measuring the measurement variable.

11. The multiple capillary-biosensor strip according to claim 10, wherein said working electrode comprises a first electrically conductive layer extending over a capillary-channel facing surface of one said wall part, and said counter electrode comprises a second electrically conductive layer extending over a capillary-channel facing surface of the other said wall part, each said layer being electrically isolated from the other along the multiple capillary-biosensor strip.

12. The multiple capillary-biosensor strip according to claim 1 or claim 2, said wall parts comprising at least an upper tape and a lower tape, each said tape generally continuously extending over the longitudinal length of the strip for delimiting the capillary channels of each consecutively provided biosensor.

13. The multiple capillary-biosensor strip according to claim 12, the capillary channels for the consecutively provided biosensors generally being in alignment such that the inlet for a following said biosensor generally oppositely faces the vent for the biosensor preceding said following biosensor, the strip further comprising a plurality of spaced apart flow obstructions provided on at least one of the wall parts, each flow obstruction being provided in conjunction with at least one capillary channel and proximate each vent-inlet interface, each said flow obstruction being configured to obstruct the flow of sample liquid through each capillary channel proximate its respective vent to prevent flow from continuing into the inlet of the following biosensor.

14. The multiple capillary-biosensor strip according to claim 13, wherein the flow obstruction comprises an aperture extending through at least one of the wall parts and over the width of the capillary channel.

15. The multiple capillary-biosensor strip according to claim 14, each said biosensor comprising an electrochemical capillary sensor having a working electrode, a counter electrode, and means for electrically connecting the working and counter electrodes to an evaluation instrument configured for measuring the measurement variable.

16. The multiple capillary-biosensor strip according to claim 15, wherein said working electrode comprises a first electrically conductive layer extending over a capillary-channel facing surface of one said wall part, and said counter electrode comprises a second electrically conductive layer extending over a capillary-channel facing surface of the other said wall part, each said layer being electrically isolated from the other along the multiple capillary-biosensor strip.

17. The multiple capillary-biosensor strip according to claim 13, each said biosensor comprising an electrochemical capillary sensor having a working electrode, a counter electrode, and means for electrically connecting the working and counter electrodes to an evaluation instrument configured for measuring the measurement variable.

18. The multiple capillary-biosensor strip according to claim 17, wherein said working electrode comprises a first electrically conductive layer extending over a capillary-channel facing surface of one said wall part, and said counter electrode comprises a second electrically conductive layer extending over a capillary-channel facing surface of the other said wall part, each said layer being electrically isolated from the other along the multiple capillary-biosensor strip.

19. The multiple capillary-biosensor strip according to claim 12, each said biosensor comprising an electrochemical capillary sensor having a working electrode, a counter electrode, and means for electrically connecting the working and counter electrodes to an evaluation instrument configured for measuring the measurement variable.

20. The multiple capillary-biosensor strip according to claim 19, wherein said working electrode comprises a first electrically conductive layer extending over a capillary-channel facing surface of one said wall part, and said counter electrode comprises a second electrically conductive layer extending over a capillary-channel facing surface of the other said wall part, each said layer being electrically isolated from the other along the multiple capillary-biosensor strip.

21. The multiple capillary-biosensor strip according to claim 1 or claim 2, the capillary channels for the consecutively provided biosensors generally being in alignment such that the inlet for a following said biosensor generally oppositely faces the vent for the biosensor preceding said following biosensor, the strip further comprising a plurality of spaced apart flow obstructions provided on at least one of the wall pans, each flow obstruction being provided in conjunction with at least one capillary channel and proximate each vent-inlet interface, each said flow obstruction being configured to obstruct the flow of sample liquid through each capillary channel proximate its respective vent to prevent flow from continuing into the inlet of the following biosensor.

22. The multiple capillary-biosensor strip according to claim 21, wherein the flow obstruction comprises an aperture extending through at least one of the wall parts and over the width of the capillary channel.

23. The multiple capillary-biosensor strip according to claim 22, each said biosensor comprising an electrochemical capillary sensor having a working electrode, a counter electrode, and means for electrically connecting the working and counter electrodes to an evaluation instrument configured for measuring the measurement variable.

24. The multiple capillary-biosensor strip according to claim 23, wherein said working electrode comprises a first electrically conductive layer extending over a capillary-channel facing surface of one said wall part, and said counter electrode comprises a second electrically conductive layer extending over a capillary-channel facing surface of the other said wall part, each said layer being electrically isolated from the other along the multiple capillary-biosensor strip.

25. The multiple capillary-biosensor strip according to claim 21, each said biosensor comprising an electrochemical capillary sensor having a working electrode, a counter electrode, and means for electrically connecting the working and counter electrodes to an evaluation instrument configured for measuring the measurement variable.

26. The multiple capillary-biosensor strip according to claim 25, wherein said working electrode comprises a first electrically conductive layer extending over a capillary-channel facing surface of one said wall part, and said counter electrode comprises a second electrically conductive layer extending over a capillary-channel facing surface of the other said wall part, each said layer being electrically isolated from the other along the multiple capillary-biosensor strip.

27. The multiple capillary-biosensor strip according to claim 1 or claim 2, each said biosensor comprising an electrochemical capillary sensor having a working electrode, a counter electrode, and means for electrically connecting the working and counter electrodes to an evaluation instrument configured for measuring the measurement variable.

28. The multiple capillary-biosensor strip according to claim 27, wherein said working electrode comprises a first electrically conductive layer extending over a capillary-channel facing surface of one said wall part, and said counter electrode comprises a second electrically conductive layer extending over a capillary-channel facing surface of the other said wall part, each said layer being electrically isolated from the other along the multiple capillary-biosensor strip.

29. The multiple capillary-biosensor strip of claim 1, the strip further comprising a plurality of spaced apart flow obstructions provided on at least one of the wall parts, each how obstruction being provided in conjunction with at least one capillary channel and being configured to obstruct the flow of sample liquid through the capillary channel to prevent flow from continuing into the inlet of the following biosensor.

30. A capillary biosensor analysis system for analyzing a sample liquid, such as a bodily fluid of humans and other animals, with respect to an analyte contained therein, comprising:

a plurality of capillary biosensors, said biosensors each including a capillary channel delimited by at least two wall parts and having an inlet for the sample liquid and a vent, the capillary channel of each said biosensor containing at least one reagent, the reaction of the sample liquid with the at least one reagent resulting in a measurable change of a measurement variable which is characteristic for the analysis;

and an evaluation instrument, said instrument comprising a holder configured for positioning one of said capillary biosensors in a measurement position for performing the analysis, said measurement position being such that said inlet of said one capillary biosensor is accessible for bringing a sample liquid to be assayed into contact with the inlet, whereby the sample liquid is drawn by capillary forces into the capillary channel; and an electrical measurement and evaluation device in said instrument for measuring the measurement variable and determining the desired analysis information on the basis of the measured value resulting from the measurement;

wherein the plurality of capillary biosensors are provided in a multiple capillary-biosensor strip comprising said plurality of capillary biosensors arranged longitudinally and consecutively provided one after the other, said multiple capillary-biosensor strip being guided and held in the holder of the evaluation instrument in such a manner that one capillary biosensor of the strip at a time is located in the measurement position and its inlet is accessible for contact with sample liquid, and said multiple capillary-biosensor strip being movable in the evaluation instrument in such a manner that consecutive capillary biosensors of the multiple capillary-biosensor strip are transported one after the other into the measurement position.

31. The capillary biosensor analysis system according to claim 30, the evaluation instrument further comprising a cutting device by which, after performing a measurement with the forward-most capillary biosensor being in the measurement position, the used forward-most capillary biosensor is cut off from the multiple capillary-biosensor strip.

32. The capillary biosensor analysis system according to claim 30 or claim 31, wherein the capillary biosensors of the multiple capillary-biosensor strip are electrochemical capillary biosensors, each of which has a working electrode, a counter electrode, and at least two conductive leads, one said conductive lead being electrically connected at its one end to the working electrode and at its other end to a first contact, another said conductive lead being electrically connected at its one end to the counter electrode and at its other end to a second contact, said first and second contacts being in electrical contact with corresponding first and second device contacts electrically connected to the electrical measurement and evaluation device.

33. The capillary biosensor analysis system according to claim 32, wherein said working electrode and said counter electrode each comprise an electrically conductive layer, each said layer being electrically isolated from the other, each said layer extending without electrical separation into each capillary biosensor along the multiple capillary-biosensor strip.

34. The capillary biosensor analysis system according to claim 33, said multiple capillary-biosensor strip being implemented as a resiliently flexible band adapted for being wound up in a curved state for being removably inserted into said evaluation instrument, the capillary channels for the consecutively provided biosensors generally being in alignment such that the inlet for a following said biosensor generally oppositely faces the vent for the biosensor preceding said following biosensor, the strip further comprising a plurality of spaced apart flow obstructions provided on at least one of the wall parts, each flow obstruction being provided in conjunction with at least one capillary channel and proximate each vent-inlet interface, each said flow obstruction being configured to obstruct the flow of sample liquid through each capillary channel proximate its respective vent to prevent flow from continuing into the inlet of the following biosensor.

35. The capillary biosensor analysis system according to claim 32, said multiple capillary-biosensor strip being implemented as a resiliently flexible band adapted for being wound up in a curved state for being removably inserted into said evaluation instrument, the capillary channels for the consecutively provided biosensors generally being in alignment such that the inlet for a following said biosensor generally oppositely faces the vent for the biosensor preceding said following biosensor, the strip further comprising a plurality of spaced apart flow obstructions provided on at least one of the wall parts, each flow obstruction being provided in conjunction with at least one capillary channel and proximate each vent-inlet interface, each said flow obstruction being configured to obstruct the flow of sample liquid through each capillary channel proximate its respective vent to prevent flow from continuing into the inlet of the following biosensor.

36. The capillary biosensor analysis system according to claim 31, said multiple capillary-biosensor strip being implemented as a resiliently flexible band adapted for being wound up in a curved state for being removably inserted into said evaluation instrument, the capillary channels for the consecutively provided biosensors generally being in alignment such that the inlet for a following said biosensor generally oppositely faces the vent for the biosensor preceding said following biosensor, the strip further comprising a plurality of spaced apart flow obstructions provided on at least one of the wall parts, each flow obstruction being provided in conjunction with at least one capillary channel and proximate each vent-inlet interface, each said flow obstruction being configured to obstruct the flow of sample liquid through each capillary channel proximate its respective vent to prevent flow from continuing into the inlet of the following biosensor.

37. The capillary biosensor analysis system according to claim 30, said multiple capillary-biosensor strip being implemented as a resiliently flexible band adapted for being wound up in a curved state for being removably inserted into said evaluation instrument, the capillary channels for the consecutively provided biosensors generally being in alignment such that the inlet for a following said biosensor generally oppositely faces the vent for the biosensor preceding said following biosensor, the strip further comprising a plurality of spaced apart flow obstructions provided on at least one of the wall parts, each flow obstruction being provided in conjunction with at least one capillary channel and proximate each vent-inlet interface, each said flow obstruction being configured to obstruct the flow of sample liquid through each capillary channel proximate its respective vent to prevent flow from continuing into the inlet of the following biosensor.

38. The capillary biosensor analysis system of claim 30, wherein each capillary channel of the multiple capillary sensor strip comprises at least one flow obstruction formed by a recess which extends through at least one of the wall parts and over the width of the capillary channel, by which flow obstruction the flow of a sample liquid entering via its inlet is stopped and the sample liquid is thus prevented from advancing into the next following capillary sensor of the multiple capillary sensor strip.

* * * * *